United States Patent [19]

Schnettler et al.

[11] Patent Number: 4,866,182

[45] Date of Patent: Sep. 12, 1989

[54] CARDIOTONIC ALKANOYL AND AROYL OXAZOLONES

[75] Inventors: Richard A. Schnettler; Winton D. Jones; Richard C. Dage, all of Cincinnati, Ohio

[73] Assignee: Merrell Dow Pharmaceuticals Inc., Cincinnati, Ohio

[21] Appl. No.: 157,430

[22] Filed: Feb. 18, 1988

[51] Int. Cl.$^4$ .................. C07D 263/38; C07D 413/12
[52] U.S. Cl. ..................................... 548/230; 546/275
[58] Field of Search ....................... 546/275; 548/230; 514/340, 376

[56] References Cited

U.S. PATENT DOCUMENTS 3,514,465  5/1970  Posselt et al. ................... 546/334
4,623,651 11/1986  Grisar et al. .................... 514/342
4,670,450  6/1987  Schnettler et al. ............... 548/182
4,689,353 10/1987  Schnettler et al. ............... 546/275
4,728,661  3/1988  Schnettler et al. ............... 514/376
4,762,849  8/1988  Grisar et al. .................... 514/369

FOREIGN PATENT DOCUMENTS 114261  4/1987  European Pat. Off. .
114262  4/1987  European Pat. Off. .
114263  4/1987  European Pat. Off. .

OTHER PUBLICATIONS

Jiro Okamiya, Chem. Abst. 65-15361 h (1966), The Preparation and the Rates of the Reaction of Heterocyclic (Thiophen and Thiazole) Bromoketones with Thioamides.

Primary Examiner—Donald G. Daus
Assistant Examiner—Cecilia Shen
Attorney, Agent, or Firm—Michael J. Sayles; Stephen L. Nesbitt

[57] ABSTRACT

Alkanoyl or aroyl oxazolones enhance myocardial contractile force and are useful as cardiotonics in the treatment of heart failure.

14 Claims, No Drawings

CARDIOTONIC ALKANOYL AND AROYL OXAZOLONES

BACKGROUND OF THE INVENTION

This invention relates to the use of certain alkanoyl and aroyl oxazolones to enhance myocardial contractile force. These compounds are useful as cardiotonics in the treatment of heart failure and are also useful as vasodilators.

Heart failure is that physiological condition resulting from the inability of the heart to maintain adequate blood flow to the peripheral body tissues and includes congestive heart failure, backward and forward heart failure, right ventricular and left ventricular heart failure, and low-output heart failure. Heart failure can be caused by myocardial ischemia, myocardial infarction, excessive alcohol usage, pulmonary embolism, infection, anemia, arrhythmias, and systemic hypertension. Symptoms include tachycardia, fatigue with exertion, dyspnea, orthopnea, and pulmonary edema.

Treatment involves either removal or correction of the underlying causes or involves control of the heart failure state. Management or control can be accomplished by increasing cardiac output or by decreasing cardiac workload. While workload can be accomplished by reduction of physical activities and physical and emotional rest, increasing cardiac output has traditionally involved digitalis therapy. Digitalis stimulates contractile force of the heart which increases cardiac output and improves ventricular emptying. In this way digitalis therapy normalizes venous pressure and reduces peripheral vasoconstriction, circulatory congestion, and organ hypoperfusion.

Unfortunately, optimal doses of digitalis vary with the patient's age, size, and condition and the therapeutic to toxic ratio is quite narrow. In most patients the lethal dose is only about five to ten times the minimal effective dose with toxic effects becoming apparent at only 1.5 to 2.0 times the effective dose. For these reasons, dose must be carefully tailored to suit the individual and frequent clinical examinations and electrocardiogram is necessary to detect early signs of digitalis intoxication. Despite this care, digitalis intoxication is reported in up to one-fifth of hospitalized patients undergoing therapy.

The need for less toxic and more effective cardiotonic agents is readily apparent. Applicants have discovered certain alkanoyl and aroyl oxazolones which possess potent cardiotonic and vasodilation activity and by comparison to digitalis have few toxic effects.

SUMMARY OF THE INVENTION

This invention relates to certain oxazolones of structure 1:

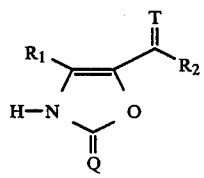

wherein
Q and T are each independently a divalent sulfur or oxygen group;
$R_1$ is a hydrogen or a $(C_1-C_4)$ alkyl group; and
$R_2$ is a $(C_1-C_6)$alkyl group or
$R_2$ is a phenyl or benzyl optionally substituted with one or two $(C_1-C_4)$ alkyl, $(C_1-C_4)$ alkoxy, $(C_1-C_4)$alkylthio, $(C_1-C_4)$alkylsulfinyl, $(C_1-C_4)$alkylsulphonyl, hydroxy, halogen, cyano, amino, mono and di$(C_1-C_4)$alkyl substituted amino, $(C_2-C_5)$alkanoylamino, carboxy, carb$(C_1-C_4)$alkoxy, carbamido, trifluoromethyl, or imidazolyl groups, or
$R_2$ is a pyridyl group optionally substituted with a $(C_1-C_4)$alkyl, $(C_1-C_4)$alkoxy, $(C_1-C_4)$alkylthio, $(C_1-C_4)$alkylsulfinyl, $(C_1-C_4)$alkylsulphonyl, hydroxy, halogen, cyano, carboxy, carb$(C_1-C_4)$ alkoxy, carbamido, trifluoromethyl, or imidazolyl group, or
$R_2$ is an indol-2-one of the formula

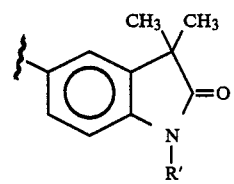

wherein R' is a hydrogen or a $(C_1-C_4)$alkyl group; or
$R_2$ is a furanyl, thienyl, or pyrryl group
and the pharmaceutically acceptably salts thereof as well as the use of these compounds as vasodilators, to enhance myocardial contractile force, and to treat heart failure, their pharmaceutical compositions, and the process of their preparation.

DETAILED DESCRIPTION OF THE INVENTION

The oxazole ring of the compounds of structure 1 exist in several tautomeric forms. Throughout this disclosure, the alkanoyl and aroyl oxazolones of structure 1 are intended to include these tautomers as well.

The ring nitrogen atom of the oxazole ring in the structure 1 compounds can be substituted with a $(C_1-C_5)$ alkyl group, an alkanoyl group such as an acetyl group, or benzoyl group. These nitrogen substituted compounds are equivalent to the unsubstituted compounds and possess significant ability to enhance myocardial contractile force.

As is true for most classes of therapeutically effective compounds, certain subclasses and certain species are more effective than others. In this instance those compounds of structure 1 wherein Q and T are a divalent oxygen group are preferred. Also preferred are those compounds wherein $R_1$ is a methyl or ethyl group and those compounds wherein $R_2$ is an optionally substituted phenyl group, a pyridyl group or a $(C_1-C_6)$alkyl group. More preferred are those compounds of structure 1 wherein $R_2$ is a 4-substituted phenyl group, especially a 4-imidazoyl substituted phenyl group. The preferred compound is 5-[4-(1H-imidazol-1-yl)benzoyl]-4-methyl-2(3H)-oxazalone.

The compounds of this invention are useful both in the free base form and in the form of acid addition salts. The acid addition salts are simply a more convenient form for use and, in practice, use of the salt amounts to use of the free base. The expression "pharmaceutically acceptable acid addition salts" is intended to apply to any non-toxic organic or inorganic acid addition salts of the base compounds of formula 1. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative of such acids are, for example, the sulfonic acids such as methane sulfonic acid and 2-hydroxyethane sulfonic acid. Either the mono- or the di-acid salts can be formed, and such salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution.

The compounds of this invention can be prepared by a Friedal-Crafts acylation of an oxazolone of formula 2:

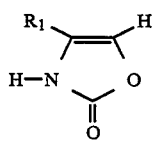

wherein $R_1$ is as defined in Formula 1. The acylating agent may be a furanoyl halide, preferably furanoyl chloride, a thienoyl halide, preferably thienoyl chloride, a pyrrol halide, preferably a pyrrol chloride, a ($C_2$–$C_7$)alkanoyl halide, preferably a ($C_2$–$C_7$)alkanoyl chloride, indol-2-onoyl halide, or a benzoyl or benzyl carbonyl halide, preferably a benzoyl or benzyl carbonyl chloride. Furthermore, the Friedel-Crafts reaction may be performed on the free acid or its corresponding acid anhydride instead of the acid halides mentioned hereinabove employing essentially identical reaction conditions. These alternate reactions are more fully described in Olah, "Friedel-Crafts and Related Reactions." Vol. III, part I, Interscience Publications, John Wiley and Sons, New York, 1964.

The Friedel-Crafts reactions of this invention are performed by premixing about 1 molar equivalent of the appropriate oxazolone with about 1 molar equivalent to about 10 molar equivalents, preferably about 2 molar equivalents, of a Lewis acid catalyst in a suitable solvent, for example, petroleum ethers; a chlorinated hydrocarbon, such as carbon tetrachloride, ethylene chloride, methylene chloride or chloroform; a chlorinated aromatic, such as 1,2,4 trichlorobenzene or o-dichlorobenzene; carbon disulfide; or nitrobenzene. Methylene chloride is preferred. About 1 molar equivalent to about 10 molar equivalents, preferably about 1.1 molar equivalents of the appropriate acid halide is added, preferably dropwise, to the mixture of oxazolones, Lewis acid, and solvent and the reaction is allowed to proceed for about ½ hour to about 100 hours, preferably from about 1 hour to about 10 hours depending on the reactants, the solvent, and the temperature which can be from about −78° to about 150° C., preferably about 0° to about 100° C., most preferably about 60° C. The resulting alkanoyl or aroyl oxazolone may be isolated from the reaction mixture by any suitable art-known procedure, preferably by quenching the reaction mixture with ice water and subsequently removing the product by filtration or extraction and solvent removal.

Lewis acid catalysts suitable for use in the Friedel-Crafts reactions described herein are, for example, a metal, salt or a strong acid, such as aluminum chloride or bromide, or an acid such as polyphosphoric acid.

The compounds of Formula 1 wherein $R_2$ is a hydroxy substituted phenyl or benzyl group can be prepared from the corresponding methoxy or benzyloxy substituted compound. The methoxy compound is cleaved to form the corresponding hydroxybenzoylimidazol-2-one by any suitable art-known procedure such as are taught by R. L. Burwell, "The Cleavage of Ethers," *Chem. Rev.* 54, 615–85 (1954). The benzyl group can be removed in the usual way by hydrogenolysis using, for example, hydrogen gas and atmospheric pressure and a palladium on carbon catalyst.

When desired, the nitrogen atom of the oxazolone ring may be substituted with an alkyl group by any art-known procedure. Such methods include reacting the appropriate N-unsubstituted oxazolone of this invention with a base and an alkylating agent in presence of an unreactive solvent. Suitable bases for this reaction can be, for example, a hydride such as sodium hydride or calcium hydride; a carbonate or bicarbonate such as sodium carbonate or sodium bicarbonate; a phenoxide such as sodium phenoxide; an alkoxide such as sodium ethoxide, or preferably a hydroxide such as sodium hydroxide. Suitable alkylating agents for this reaction are, for example, a alkyl halide such as methyl chloride, methyl bromide, or methyl iodide; or a dialkylsulfate such as dimethylsulfate. Suitable unreactive solvents are, for example, petroleum ethers; chlorinated hydrocarbons such as carbon tetrachloride, chloroform, or methylene chloride; chlorinated aromatics such as 1,2,4-trichlorobenzene, o-dichlorobenzene, or chlorobenzene; carbon disulfide; nitrobenzene; ethereal solvents such as diethyl ether, tetrahydrofuran or p-dioxan; aromatic solvents such as benzene, toluene or xylene; or preferably the polar aprotic solvents such as dimethylformamide (DMF) or dimethylsulfoxide (DMSO). The reaction is allowed to proceed from about 1 minute to about 1 hour and the temperature may be from about 0° to about 100° C., preferably about 25° C. The appropriate oxazolone is reacted with from about 2 molar equivalents to about 10 molar equivalents of a base, preferably about 2 molar equivalents and from about 2 molar equivalents to about 10 molar equivalents of an alkylating agent, preferably about 2 molar equivalents. Finally, any reactive substituents on the aroyl rings, for example, a hydroxy group, may become alkylated concurrently. If desired, the alkylation of the aroyl ring substituents may be avoided by the use of suitable protecting groups well known in the art.

When desired, the nitrogen atom of the oxazolone ring may be substituted with an alkylcarbonyl or benzoyl group by any suitable art-known procedure. Such methods include reacting the N-unsubstituted 2-oxazolone of this invention with an acyl halide, preferably an acyl chloride such as acetyl chloride, n-propanoyl chloride, isopropanoyl chloride or butanoyl chloride. Normally, acylation reactions utilizing acyl halides employ an acid sponge such as triethylamine or pyridine to remove any hydrohalide as it is formed. Furthermore, the corresponding free acid or acid anhydride may be employed instead of the acyl halides. Acylation reactions are generally run without added solvent but may be performed using any nonreactive solvent, for example, petroleum ethers; chlorinated hydrocarbons such as chloroform, methylene chloride or carbon tetrachloride; carbon disulfide; or the ethereal solvents, such as diethylether, tetrahydrofuran or p-dioxan. The reactions are allowed to proceed for about 1 minute to about 100 hours, preferably from about 1 hour to about 10 hours and the temperature may be from about −78° to about 150° C., preferably from 0° to 100° C. Finally, any reactive substituents on the aroyl rings, such as a hydroxy group, will become acylated concurrently. If desired, the acylation of the benzoyl ring substituents may be avoided by the use of suitable protecting groups well-known in the art.

The compounds of structure 1 are cardiotonic and vasodilator agents useful in the treatment of heart failure and are believed to function by strengthening the heart muscle by virtue of their ability to enhance myocardial contractile force and reducing work load by virtue of their vasodilator activity. The utility of the structure 1 compounds as cardiotonic agents may be determined by administering the test compound (0.1-100 mg/kg) intraveneously, intraperitoneally, intraduodenally, or intragastrically in a suitable vehicle to a mongrel dog (either sex). The test dogs are anesthetized and prepared by isolating a suitable artery (e.g., femoral or common carotid) and vein (e.g., femoral or external jugular) and introducing polyethylene catheters filled with 0.1% Heparin-Sodium to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. A catheter may also be put into the left atrium or the left ventricle of the heart to record left atrial pressure or left ventricular pressure. Heart failure is induced by administering sodium pentobarbital (20 to 40 mg/kg) followed by a continuous infusion of 0.25-2 mg/kg/min. or propranolol hydrochloride (4 mg/kg) followed by a continuous infusion of 0.18 mg/kg/min. to the blood perfusing the heart. Following administration of either of the cardiac depressants, the right atrial pressure dramatically increases and cardiac output is severely depressed. Reversal of these effects by the test compound indicates cardiotonic activity.

The amount of the active ingredient to be administered can vary widely according to the particular dosage unit employed, the period of treatment, the age and sex of the patient treated, and the nature and extent of the disorder treated. The total amount of the active ingredient to be administered will generally range from about 0.1 mg/kg to 100 mg/kg and preferably from 0.3 mg/kg to 10 mg/kg. A unit dosage may contain from 15 to 500 mg of active ingredient, and can be taken one or more times per day. The active compound of formula 1 can be administered with a pharmaceutical carrier using conventional dosage unit forms either orally, parenterally, or topically.

As used herein, the term "patient" is taken to mean warm blooded animals, for example, birds such as chickens and turkeys, and mammals such as sheep, horses, cattle, pigs, dogs, cats, rats, mice, and primates including humans.

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The active ingredient may also be administered by means of a sustained release system whereby the compound of formula 1 is gradually released at a controlled, uniform rate form an inert or bioerodible carrier by means of diffusion, osmosis, or disintegration of the carrier during the treatment period. Controlled release drug delivery systems may be in the form of a patch or bandage applied to the skin or to the buccal, sublingual, or intranasal membranes, or a gradually eroding tablet or capsule or a gastrointestinal reservoir administered orally. Administration by means of such sustained release delivery systems permits the tissues of the body to be exposed constantly for a prolonged time period to a therapeutically or prophylactically effective dosage of a compound of formula 1. The unit dosage of the compound administered by means of a sustained release system will approximate the amount of an effective daily dosage multiplied by the maximum number of days during which the carrier is to remain on or in the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polyalcohols, polyethers, polyesters, polyurethanes, polysulphones, polysiloxanes, and polyimides as wells as mixtures and copolymers of these polymers. The compounds of formula 1 may be incorporated in the sustained release carrier in a pure form or may be dissolved in any suitable liquid or solid vehicle, including the polymer of which the sustained release carrier is formed.

EXAMPLES

The following specific examples illustrate the preparation of the compounds of this invention as well as the pharmaceutical compositions containing these compounds but are not intended to limit the scope of the invention.

EXAMPLE 1

Preparation of 5-[4-(1H-imidazol-1-yl)benzoyl]-4-methyl-2(3H)-oxazolone

In 50 ml methylene chloride were placed 1.30 g (0.0132 mol) 4-methyl-2(3H)-oxazolone and 5.22 g (0.039 mol) aluminum chloride. The mixture was stirred 30 minutes and 2.72 g (0.0132 mol) 4-(1H-imidazol-1-yl)benzoyl chloride were added. The mixture was heated on the steam bath allowing the methylene chloride to evaporate, after which the residue was heated an additional 30 minutes. The residue was quenched with water and the water solution neutralized with sodium bicarbonate. The solution was evaporated to dryness and the residue was leached with hot methanol. Evaporation of the methanol provided the crude product which was purified by chromatography; m.p. 320°.

Anal. Calcd. for $C_{14}H_{11}N_3O_3$: C, 62.44; H, 4.11; N, 15.60. Found: C, 62.17; H, 4.11; N, 15.61.

EXAMPLE 2

Preparation of 5-n-pentanoyl-4-methyl2(3H)oxazolone

Six grams (0.06 mol) of 4-methyl-2(3H)-oxazolone and 24.2 g (0.182 mol) aluminum chloride were suspended in 250 ml methylene chloride. To this mixture was added dropwise 8.3 g (0.069 mol) n-pentanoyl chloride. The mixture was stirred and refluxed 15 hours, cooled and poured into ice water. The methylene chloride layer was isolated, washed with sodium bicarbonate solution and water. The methylene chloride solution was dried and solvent evaporated to give a residue which was recrystallized two times from ethyletherpentane to give 4.3 g (39%) of title compound; m.p. 92°-94°.

Anal. Calcd. for: $C_9H_{13}NO_3$: C, 59.00; H, 7.15; N, 7.65. Found: C, 59.00; H, 7.03; N, 7.22.

EXAMPLE 3

Preparation of 4-methyl-5-(4-pyridinyl)carbonyl-2(3H-oxazolone

In 250 ml methylene chloride were placed 10.0 g (0.1 mol) 4-methyl-2(3H)oxazolone and 32.4 g (0.24 mol) aluminum chloride. The mixture was stirred 30 minutes and 16.2 g (0.115 mol) isonicotinoyl chloride in methylene chloride were added. The solvent was allowed to boil off the stirred mixture and the mixture was heated to 120° for one hour, cooled and quenched with water. The aqueous solution was neutralized with sodium bicarbonate to pH 4. The solution was evaporated and the residue leached with ethanol until all the organic matter was dissolved. The ethanol was filtered and concentrated to 80 ml. On cooling, crystallization occurred. Repeat recrystallization from EtOH gave the title compound; m.p. 243°-245°.

Anal. Calcd for : $C_{10}H_8N_2O_3$: C, 58.82; H, 3.95; N, 13.72. Found: C, 58.74; H, 3.92; N, 13.45.

EXAMPLE 4

4-Methyl-5-(4-pyridinyl)thiocarbonyl)-3H-oxazol-2-one 10 g of 4-methyl-5-(4-pyridinyl)carbonyl-3H-oxazol-2-one is heated with phosphoruspentasulfide for 5 hours in 100 ml toluene. Evaporation of the solvent gives the title compound.

EXAMPLE 5

Preparation of 4-methyl-5-(4-pyridinyl)carbonyl-3H-oxazol-2-thione

A. 2-Bromo-2-(4-pyridyl)-1,3-butadione

To a solution of 16.3 g (0.1 mole) of 1-(4-pyridyl)-1,3-butadione in 100 ml, 48% hydrobromic acid is slowly added 15.98 g (0.1 mol) bromine. The solution is stirred until the bromine color is discharged. The solution is evaporated to dryness to give the title compound.

B. 2-Acetoxy-1-(4-pyridyl)-1,3-butadione

In 250 ml acetonitrile is dissolved 24.2 g (0.1 mol) 2-bromo-1-(4-pyridyl)-1,3-butadione and 1.2 g (0.020 mol) and dibenzo-18-crown, 19.6 g (0.2 mol) potassium acetate. The mixture is refluxed 5 hours, cooled and filtered. The filtrate is concentrated and placed on a silica gel column to purify the compound.

C. 2-Hydroxy-1-(4-oyridyl)-1,3-butadione

A solution of 22.1 g (0.1 mol) 2-acetoxy-1-(4-pyridyl)-1,3-butadione and 100 ml 6N hydrochloric acid is refluxed for 2 hours and then the solvent is evaporated to give the title compound.

D. 4-Methyl-5-(4-pyridinyl)carbonyl-3H-oxazol-2-thione

In 100 ml water is dissolved 17.9 g (0.1 mol) 2-hydroxy-1-(4-pyridyl)-1,3-butadione and 19.4 g (0.2 mol) potassium thiocyanate. The mixture is heated on the steam bath for 1 hour and cooled. Evaporation of the water causes the product to separate which is purified by crystallization from alcohol.

EXAMPLE 6

Tablets are prepared each having the composition:

|  |  |
|---|---|
|  | 250 mg |
| starch | 40 mg |
| talc | 10 mg |
| magnesium stearate | 10 mg |

EXAMPLE 7

Capsules are prepared each having the composition:

|  |  |
|---|---|
|  | 400 mg |
| talc | 40 mg |
| sodium carboxymethylcellulose | 40 mg |
| starch | 120 mg |

We claim:

1. A compound of the structure:

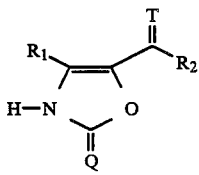

wherein
Q and T are each independently a divalent sulfur or oxygen group;
$R_1$ is a hydrogen or a $(C_1-C_4)$alkyl group; and
$R_2$ is a $(C_1-C_6)$alkyl group or
$R_2$ is a phenyl or benzyl optionally substituted with one or two $(C_1-C_4)$alkyl, $(C_{-}C_4)$alkoxy, $(C_1-C_4)$alkylthio, $(C_1C_4)$alkylsulfinyl, $(C_1-C_4)$alkylsulphonyl, hydroxy, halogen, cyano, amino, mono and di $(C_1-C_4)$alkyl substitued amino, $(C_2-C_5)$alkanoylamino, carboxy, carb$(C_1-C_4)$alkoxy, carbamido, trifluoromethyl, or imidazolyl groups, or
$R_2$ is a pyridyl group optionally substituted with a $(C_1-C_4)$alkyl, $(C_1-C_4)$alkoxy, $(C_1-C_4)$alkylthio, $(C_1-C_4)$alkylsulfinyl, $(C_1-C_4)$alkylsulphonyl, hydroxy, halogen, cyano, carboxy, carb$(C_1-C_4)$alkoxy, carbamido, trifluoromethyl, or imidazolyl group, or
$R_2$ is an indol-2-one of the formula

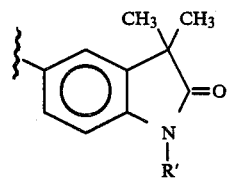

wherein $R''$ is a hydrogen or a $(C_1-C_4)$alkyl group; or
$R_2$ is a furanyl, thienyl or pyrryl group
and the pharmaceutically acceptably salts thereof.

2. A compound of claim I wherein Q and T are each a divalent oxygen group.

3. A compound of one of claims 1 or 2 wherein $R_2$ is a phenyl group optionally substituted with one or two $(C_1-C_4)$alkyl, $(C_1-C_4)$alkoxy, $(C_1C_4)$alkylthio, $(C_1-C_4)$alkylsulfinyl, $(C_1-C_4)$alkylsulphonyl, hydroxy, halogen, cyano, carboxy, carb$(C_1-C_4)$alkoxy, carbamido, trifluoromethyl, or imidazolyl groups.

4. A compound of claim 3 wherein $R_1$ is a methyl or ethyl group.

5. A compound of one of claims 1 or 2 wherein $R_2$ is a pyridyl group optionally substituted with a $(C_1-C_4)$alkyl, $(C_1-C_4)$alkoxy, $(C_1-C_4)$alkylthio, $(C_1-C_4)$alkylsulfinyl, $(C_1-C_4)$alkylsulphonyl, hydroxy, halogen, cyano, carboxy, carb$(C_1-C_4)$alkoxy, carbamido, trifluoromethyl, or imidazolyl group.

6. A compound of claim 5 wherein $R_1$ is a methyl or ethyl group.

7. A compound of one of claims 1 or 2 wherein $R_2$ is a phenyl group optionally substituted at the 4-position with a $(C_1-C_4)$alkyl, $(C_1-C_4)$alkoxy, $(C_1-C_4)$alkylthio, $(C_1-C_4)$alkylsulfinyl, $(C_1-C_4)$alkylsulphonyl, hydroxy, halogen, cyano, carboxy carb$(C_1-C_4)$alkoxy, carbamido, trifluoromethyl, or imidazolyl group.

8. A compound of one of claims 1 or 2 wherein $R_2$ is a phenyl group substituted with an imidazoyl group.

9. A compound of claim 8 wherein $R_1$ is a methyl or ethyl group.

10. A compound of one of claims 1 or 2 wherein $R_2$ is a phenyl group substituted at the 4-position with an imidazoyl group.

11. A compound of claim 10 wherein $R_1$ is a methyl or ethyl group.

12. A compound of one of claims 1 or 2 which is 5-[4-(1$\underline{H}$-imidazol-1-yl)benzoyl]-4-methyl-2(3$\underline{H}$)-oxazolone.

13. A compound of one of claims 1 or 2 wherein $R_2$ is a $(C_1-C_6)$alkyl group.

14. A compound of claim 13 wherein $R_1$ is a methyl or ethyl group.

* * * * *